US011564766B2

(12) United States Patent
Savage et al.

(10) Patent No.: US 11,564,766 B2
(45) Date of Patent: Jan. 31, 2023

(54) COMPACTOR AND DIVERTER FOR RETURN ITEMS IN A DISPENSING SYSTEM

(71) Applicant: Cintas Corporate Services, Inc., Cincinnati, OH (US)

(72) Inventors: John Savage, Cincinnati, OH (US); Brett Baylor, Green Bay, WI (US); Aaron Gallegos, Neenah, WI (US); Dale Helgren, Green Bay, WI (US); Scott Schroeder, Green Bay, WI (US)

(73) Assignee: Cintas Corporate Services, Inc., Cincinnati, OH (US)

( * ) Notice: Subject to any disclaimer, the term of this patent is extended or adjusted under 35 U.S.C. 154(b) by 0 days.

(21) Appl. No.: 17/090,967

(22) Filed: Nov. 6, 2020

(65) Prior Publication Data

US 2022/0142728 A1 May 12, 2022

(51) Int. Cl.
*A61B 50/37* (2016.01)
*B30B 9/30* (2006.01)

(52) U.S. Cl.
CPC ............ *A61B 50/37* (2016.02); *B30B 9/3003* (2013.01); *B30B 9/3082* (2013.01)

(58) Field of Classification Search
CPC ........... A61B 50/37; B30B 9/30; B30B 9/301; B30B 9/3021; B30B 9/3032; B30B 9/3046; B30B 9/305; B30B 9/306; B30B 9/3082; B30B 9/3042; B30B 15/16; B65F 1/1405
USPC .............................. 100/229 A, 228, 226, 233
See application file for complete search history.

(56) References Cited

U.S. PATENT DOCUMENTS

| 4,147,100 | A | * | 4/1979 | Dykstra | B30B 9/30 100/48 |
|---|---|---|---|---|---|
| 4,552,061 | A | * | 11/1985 | Brutsman | B30B 9/30 100/229 A |
| 4,598,810 | A | | 7/1986 | Shore et al. | |
| 5,139,205 | A | * | 8/1992 | Gallagher | B02C 18/0007 241/101.2 |
| 5,213,272 | A | * | 5/1993 | Gallagher | B30B 9/30 241/33 |
| 5,713,270 | A | | 2/1998 | Fitzgerald et al. | |
| 5,829,349 | A | | 11/1998 | Fitzgerald et al. | |
| 5,884,556 | A | * | 3/1999 | Klepacki | B65F 1/1426 100/349 |
| 6,330,856 | B1 | | 12/2001 | Fitzgerald et al. | |
| 6,418,841 | B1 | * | 7/2002 | Little | B30B 9/3007 100/229 A |

(Continued)

FOREIGN PATENT DOCUMENTS

WO WO-2009049835 A1 * 4/2009 ........... B30B 9/3053

*Primary Examiner* — Shelley M Self
*Assistant Examiner* — Smith Oberto Bapthelus
(74) *Attorney, Agent, or Firm* — Wood Herron & Evans LLP

(57) ABSTRACT

A scrubs returns cabinet for a hospital allows workers to return surgical garment tops and bottoms. A cabinet housing has a loading door leading to a return port through which the customer places the soiled scrub suit after entering customer identification information. The scrubs fall into a collection area and are dispersed by a diverter into the collection area. Additionally, a compacting paddle compacts the accumulating scrubs to utilize more of the collection area and accommodate more dirty scrubs before the collection area needs to be emptied. The scrubs are compressed by the compactor after being dispersed by the diverter.

10 Claims, 12 Drawing Sheets

(56) References Cited

U.S. PATENT DOCUMENTS

| | | |
|---|---|---|
| 6,439,500 B1 | 8/2002 | Shoenfeld |
| 7,474,938 B2 | 1/2009 | Poliner |
| 2005/0061167 A1* | 3/2005 | Fox ................... B30B 9/3021 100/215 |
| 2008/0041246 A1* | 2/2008 | Fox ................... B30B 9/3021 100/229 A |
| 2009/0145309 A1* | 6/2009 | Fox ................... B30B 9/3082 100/35 |
| 2011/0100235 A1* | 5/2011 | Hrubetz ............ B30B 9/3021 100/35 |
| 2011/0304433 A1* | 12/2011 | Molewyk ............ D06F 93/00 340/10.1 |

\* cited by examiner

COMPACTOR AND DIVERTER FOR RETURN ITEMS IN A DISPENSING SYSTEM

BACKGROUND OF THE INVENTION

This invention relates to an apparatus for receiving and compacting articles, and more particularly to an apparatus for accepting and directing garments into a compartment and compacting them therein.

Scrub garments are uniforms typically worn by doctors, nurses, and other medical workers in hospital operating rooms or other locations where the workers are likely to be in immediate proximity with patients. These scrub garments are hereafter called "scrubs". Scrubs provide an easily-changed launderable barrier between the wearer and the patient, helping to prevent the patient from exposure to germs or infectants on the wearer's body or street clothing, and also helping to protect the wearer's body from direct physical contact with a patient.

Scrubs usually are two-piece garments, consisting of a top or shirt and a bottom or pants. The tops and bottoms are stocked in different sizes to accommodate the needs of individual wearers. Scrub jackets also are worn by doctors and others. Soiled scrubs are collected for laundering and subsequent reuse, but scrubs must be periodically replaced due to wear and tear encountered in normal use as well as the effects of repeated launderings using the high temperatures and detergents required to clean and sterilize the soiled scrubs.

Hospitals normally make scrubs available to doctors and other medical workers at no direct cost to those users. Although each user is supposed to have only a limited number of scrubs at any given time for his or her personal use, some users will hoard scrubs of their size to maintain their own personal reserve. Other users may appropriate extra sets of scrubs for their own personal use, at home or elsewhere outside the hospital. These and other improper uses of scrubs contribute to an unacceptable shrinkage in the inventory of scrubs maintained by the institution for use by authorized persons.

Some hospitals try to control the distribution of scrubs by requiring users to check out scrubs from personnel at central locations. Using this approach, each authorized individual is permitted to have no more than a certain number of scrubs in his or her possession at any time. The individual must return soiled scrubs to receive credit for clean scrubs. Although this approach can alleviate the problems mentioned above, it is expensive to maintain. Many hospitals are large enough to require several scrub-dispensing locations throughout the hospital. Furthermore, because hospitals never close, scrub dispensing locations must be staffed around the clock. The direct and indirect labor costs of that staffing add significantly to the overall cost of maintaining an adequate inventory of scrubs.

Regarding the collection of soiled scrubs, manual collection suffers the disadvantage of human error, forgetfulness, and the like. When the hospital personnel doff the garments, or when the scrubs become soiled or contaminated, they are expected to return them. Often this involves simply tossing the garments into a laundry basket, or else onto the floor, and with no control over who has or has not returned their scrub suits. Recently, there has been an effort to use a scrub return facility to account for these garments. Dispensers and return units may be tied to a network in the hospital laundry facility to keep track of the numbers and sizes of scrub tops and bottoms checked out to each of the hospital personnel, and to alert laundry personnel when a dispenser is running out of garments, if the returns unit is full, or if a machine becomes jammed or inoperative for some reason. There is a need for an automated operating and tracking system that would identify a user by a unique identification means, and associate the garments that user turns in for collection. Tracking of those garments would need to correlate with subsequent issuance of clean garments so that only those users which have turned in their scrubs can obtain new ones. Such a system would reduce the number of scrubs lost or stolen. One such system is disclosed in U.S. Pat. No. 7,474,938, which is hereby incorporated by reference in its entirety.

Because the accumulation of a large number of scrubs in a collection area can result in a surprisingly large volume of material, it would be desirable to have a system that would automatically compact the scrubs in the collection area to preserve space, which is frequently in short supply at hospitals. The system disclosed in the above-identified '938 patent does not include a means to compact an accumulation of returned items. As such, the unit requires frequent attention to empty the bin of returned items for cleaning and processing.

The clothing collection apparatus shown in U.S. Pat. Nos. 5,713,270 and 5,829,349, each of which is hereby incorporated by reference in its entirety, also reduces inventory loss. Scrubs are checked in by the user, and a processor sends a credit to the user's account via a communications network. Thus, the return of a scrubs increases the scrubs available to that user from a scrubs vending machine also linked to the network.

Adapting the garment receiving apparatus of the unit shown in U.S. Pat. Nos. 5,713,270 and 5,829,349 into a compact unit presents difficulties, because a compactor by which the garments are compacted according to the '270 and '349 patents is shaped as a sweeping, vertical sheet metal device. Only the edge of the flat sheet contacts the pile of returned garments. Thus, the effective volume of clothing that the collection area can hold is limited by the limited contact area of the edge of the device. To increase the capacity of a garment collection compartment, a compaction system is needed that can more effectively move and compact garments into a larger portion of the collection compartment.

This invention relates to devices and techniques for vending or dispensing and receiving articles, and is especially directed to a returns cabinet in which hospital garments, i.e., scrubs can be received and held until they can be taken to a laundry facility.

SUMMARY OF THE INVENTION

These and other objectives of the invention have been attained by a diverter and compactor for use in a dispensing and receiving system for scrubs or other items according to various embodiments of this invention.

In accordance with aspects of this, a returns cabinet receives hospital garments or scrubs to be picked up and laundered, and credits the customer with the return. In the housing of the returns cabinet there is a return portal with a loading door for the customer to place the hospital garment(s) to be returned in the cabinet. The customer inputs unique user information via a keypad and/or a badge and card reader to allow the loading door to be opened. This enters the customer's ID, as well as an identification of the scrubs being returned. Within the cabinet housing is a system that disperses the scrubs and compresses them in a collection area until they can be discharged to or retrieved by the laundry attendant.

The returns cabinet may contain a controller that is coupled to the customer input device (keypad or badge reader) and to the drive motor. This controls the movement of the compactor such that garments received into the cabinet are dispersed by a diverter and compacted by the compactor. The compression of the soiled scrubs by the compactor is extremely effective in increasing the effective storage capacity of the returns unit or cabinet.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein.

DETAILED DESCRIPTION OF THE INVENTION

Figure 1:
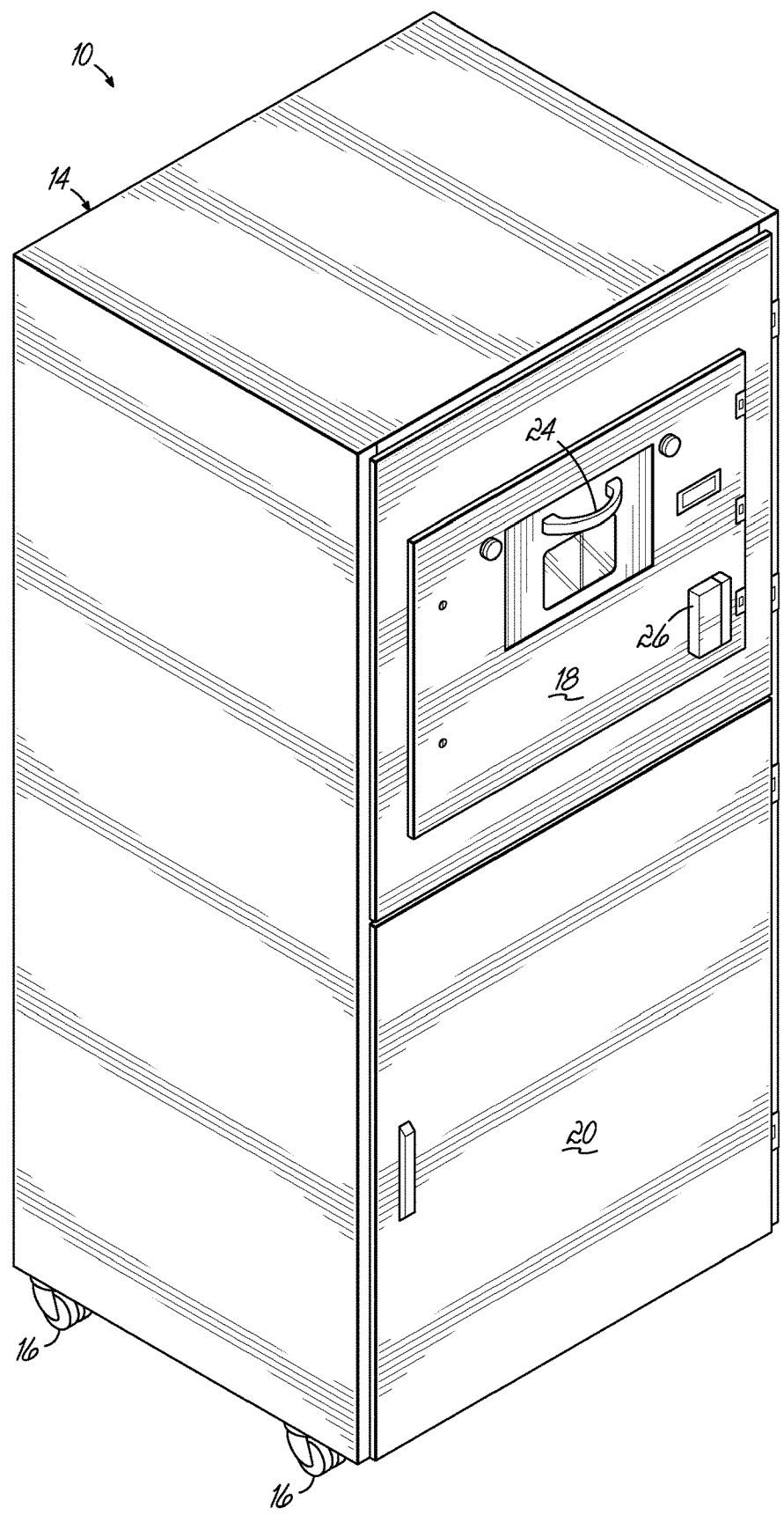
FIG. 1 is a perspective view of a returns cabinet according to one embodiment of this invention.

Referring to FIG. 1, one embodiment of a returns cabinet 10 for use in conjunction with a dispensing system according to this invention is shown. The dispensing system may be according to that which is disclosed in U.S. Pat. No. 7,474,938 or another compatible or appropriate dispensing system. The returns cabinet 10 according to various embodiments of this invention could be used to receive used, worn, soiled or other items 12 which are reusable, particularly textile materials such as scrubs used in a hospital environment. The returns cabinet 10 receives the items or scrubs 12 from a user and credits the user's account with the return of those items to allow for new or additional items or scrubs 12 to be issued to the particular user.

The returns cabinet 10 as shown in FIG. 1 includes an outer housing 14 and may be supported on multiple rollers or wheels 16 for convenient movement of the returns cabinet 10, as needed. The returns cabinet 10, as previously stated, may be used in conjunction with the dispensing system and therefore appropriately positioned and coupled for operation in connection with the dispensing system. The returns cabinet 10 includes a loading door 18 for receiving the items 12 being returned. The loading door 18 is typically positioned on an upper portion of the front face of the returns cabinet 10. A lower door 20 is likewise included on the returns cabinet housing 14 through which an operator may access a collection bin or area 22 in the housing 14 where the items 12 previously returned are held until being collected by an operator. Both the loading door 18 and the collection door 20 may include appropriate locking mechanisms to prevent or inhibit an unauthorized user from accessing the interior of the returns cabinet 10.

Figure 7A:
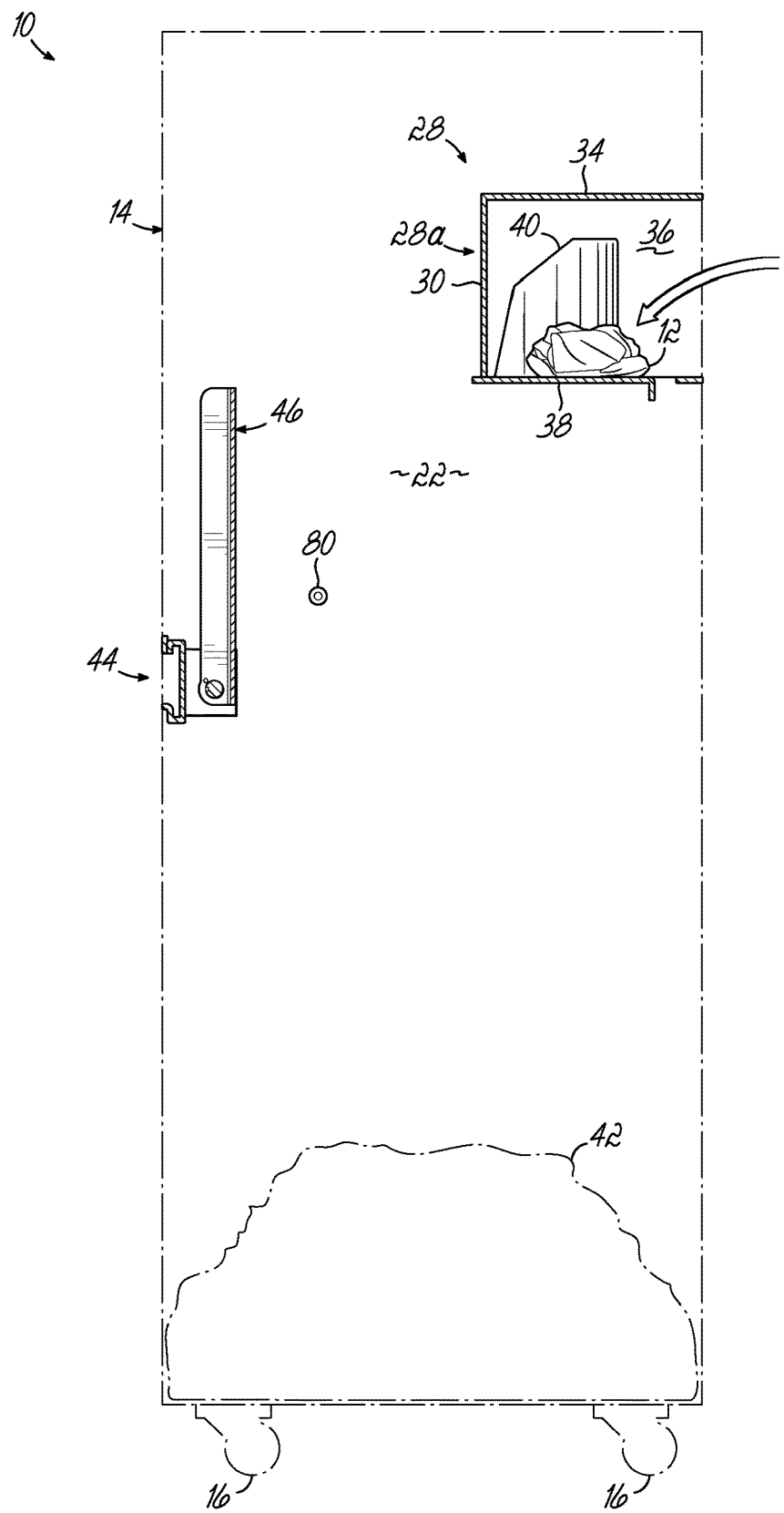
FIGS. 7A-7D are sequential side elevational views of a return portal with a diverter as well as a collection compartment relative to the compactor assembly according to one embodiment of this invention.

The loading door 18 may include a convenient handle 24 for an operator to grasp and pivot the door 18 to an open position for depositing the scrubs 12 into the return portal 28 as shown generally in FIG. 7A. A card reader, keypad or other data entry device 26 may be utilized by an operator to return scrubs or other items 12. The operator may input their unique identification information into the data entry device 26 so that the system credits the operator for returning the returned items 12. The returns cabinet 10 may be operated in conjunction with the dispensing system via a control system which operably connects to the card reader or other input device 26. Alternatively, the returns cabinet 10 may be operated independently from the dispensing system.

As shown generally in FIGS. 7A-10C, the loading door 18 when open provides access to a return portal 28 positioned behind the loading door 18. The return portal 28 defines an area into which a user may deposit scrubs 12 or other items being returned. The return portal 28 may be divided into left and right portions 28a, 28b, each of which may be utilized to receive scrubs bottoms or the scrubs tops. The return portal 28 has a volume defined by a common back wall 30, opposite side walls 32 and a common top wall 34. A central partition 36 may divide the return portal 28 into the two portions 28a, 28b. The return portal 28 includes a bottom wall 38 to support the scrubs 12 when deposited into the return portal 28. The central partition 36 allows the items 12 placed in the portion 28a to be deposited into a first portion 22a of the collection area 22 and the items 12 placed in the portion 28b to be deposited into a second portion 22b of the collection area 22 which may be initially spaced from and discrete relative to the first portion 22a of the collection area 22 to thereby allow for enhanced distribution of the items 12 in the collection area 22.

Figure 7B:
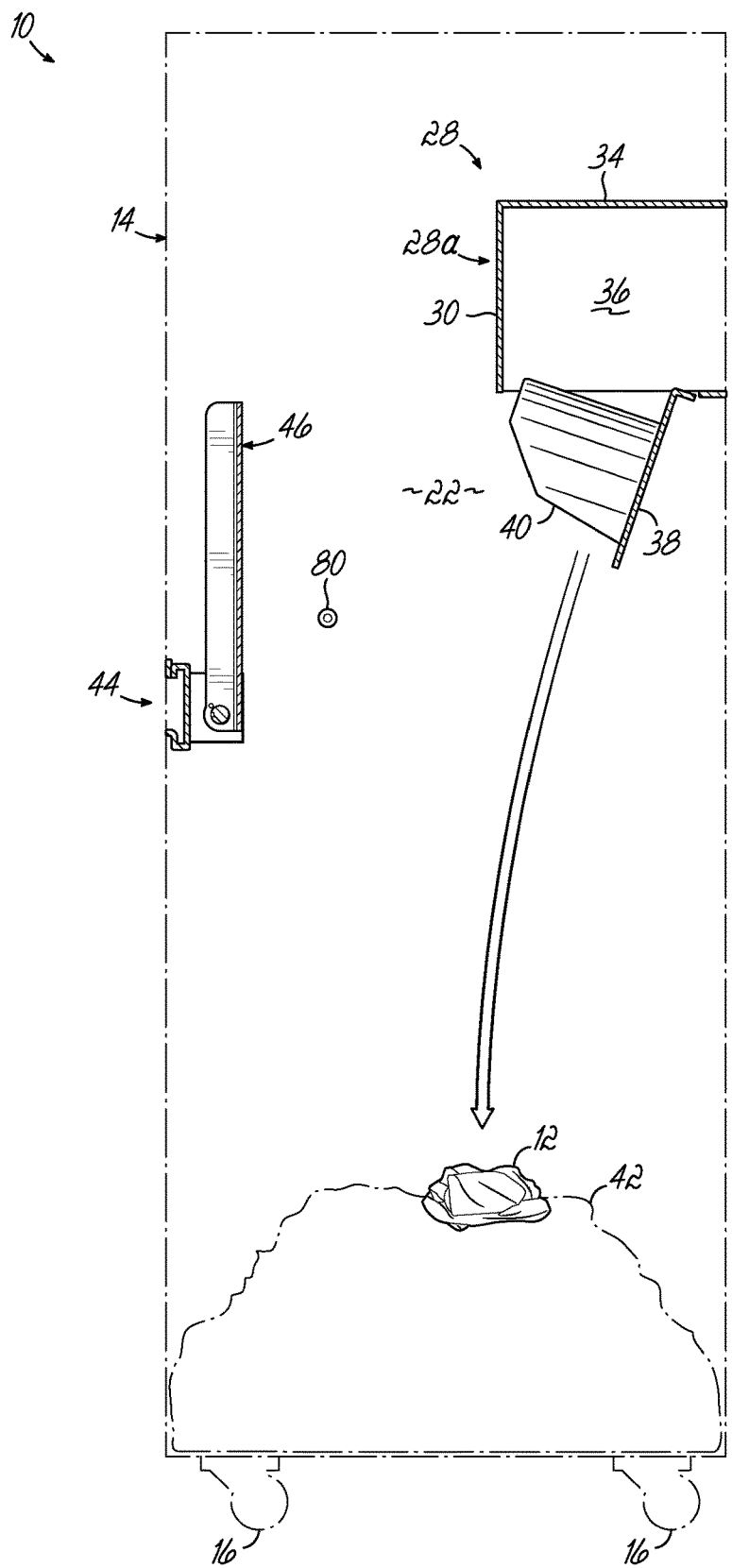
Figure 7C:
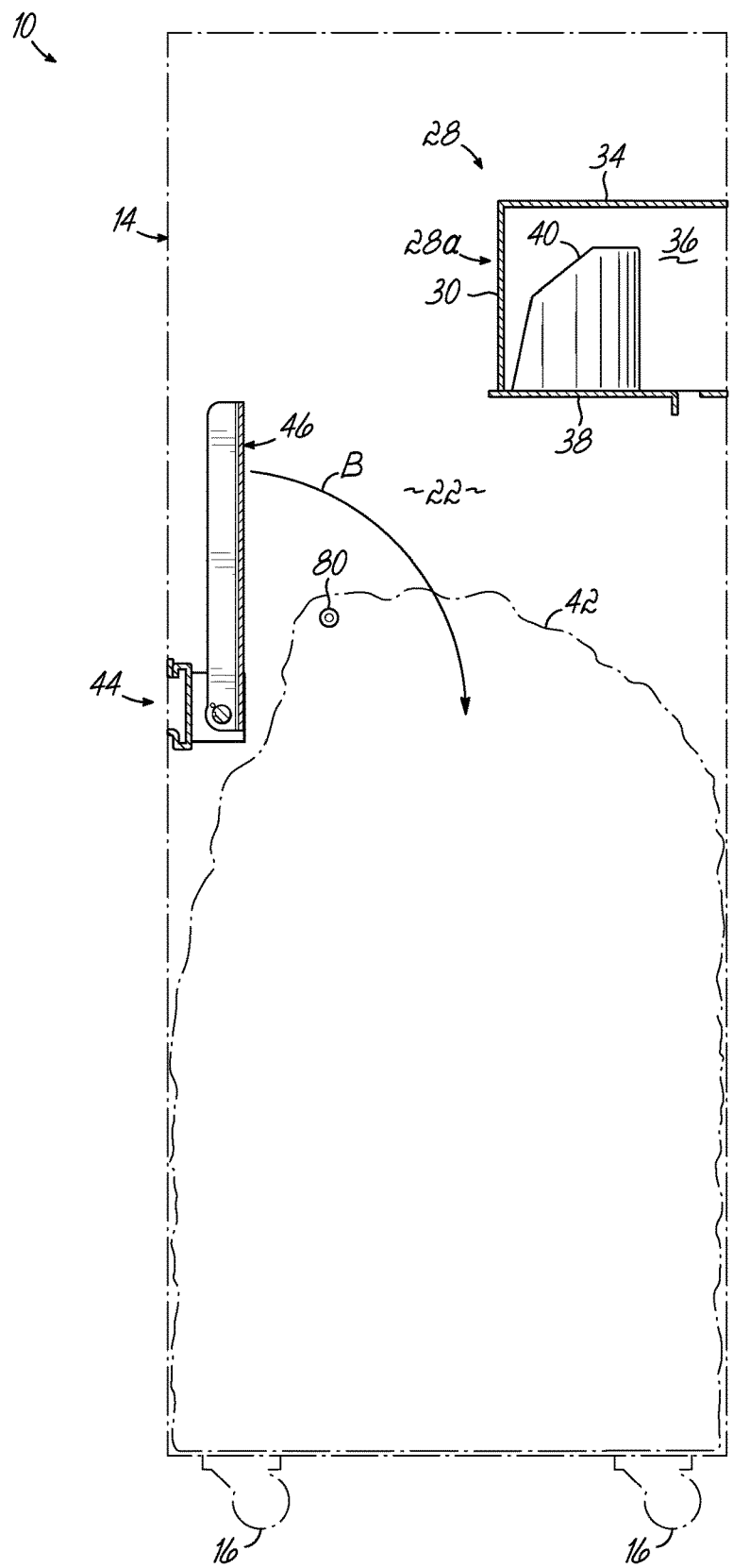

Once the loading door 18 is closed, the return portal bottom 38 may pivot downwardly as shown in FIG. 7B to thereby deposit the scrubs 12 into the collection area 22 at the bottom of the returns cabinet 10. The return portal bottom wall 38 may pivot downwardly as shown in FIG. 7B once the loading door 18 is closed and returned to its generally horizontal position as shown in FIG. 7C to be ready receive additional scrubs 12 being returned.

Figure 8:
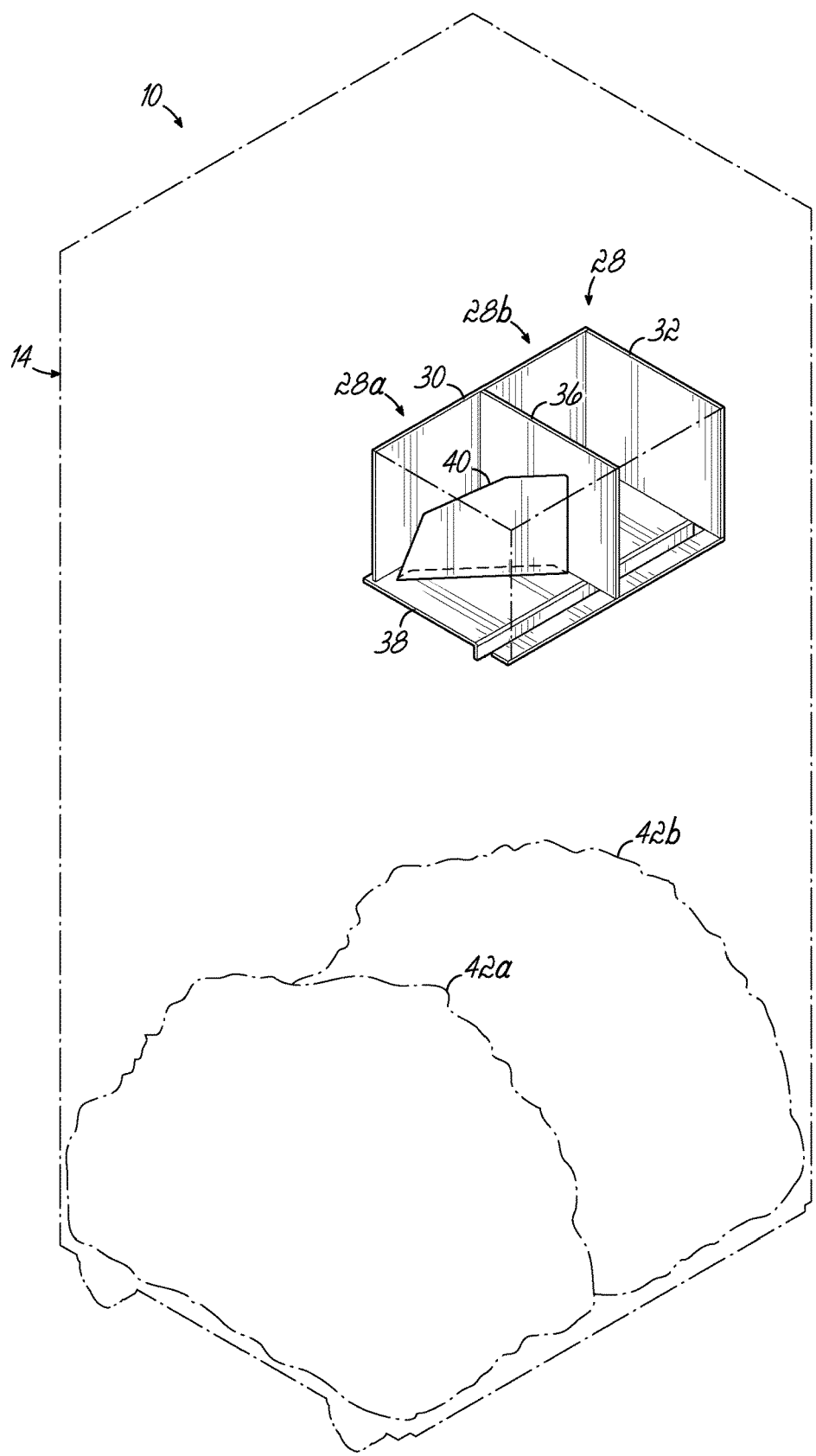
FIG. 8 is a perspective view of one embodiment of the return portal and diverter according to this invention.
Figure 9:
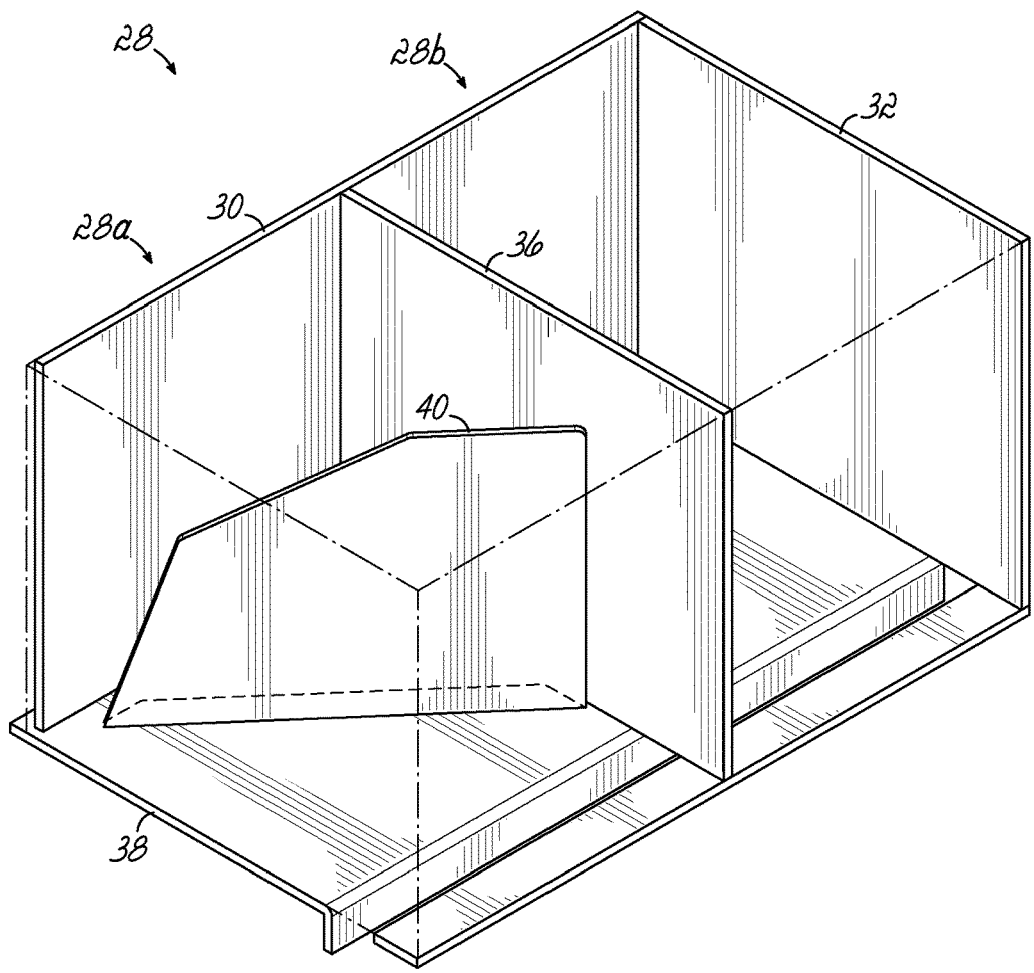
FIG. 9 is an enlarged perspective view of the return portal and diverter of FIG. 8.
Figure 10A:
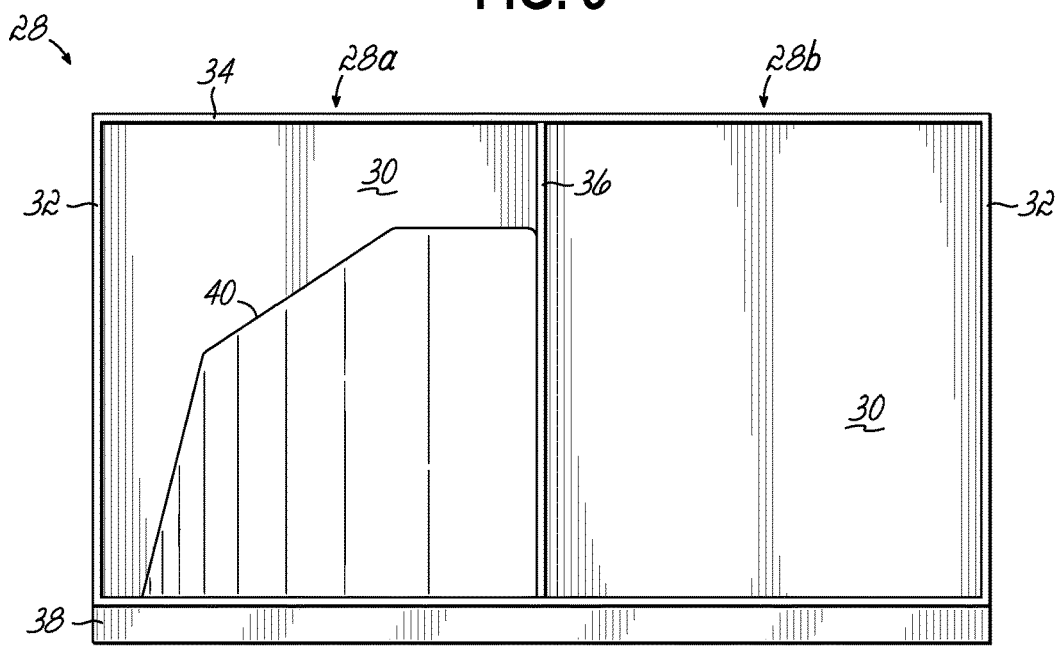
FIG. 10A is a front elevational view of the return portal and diverter of FIG. 9.
Figure 10B:
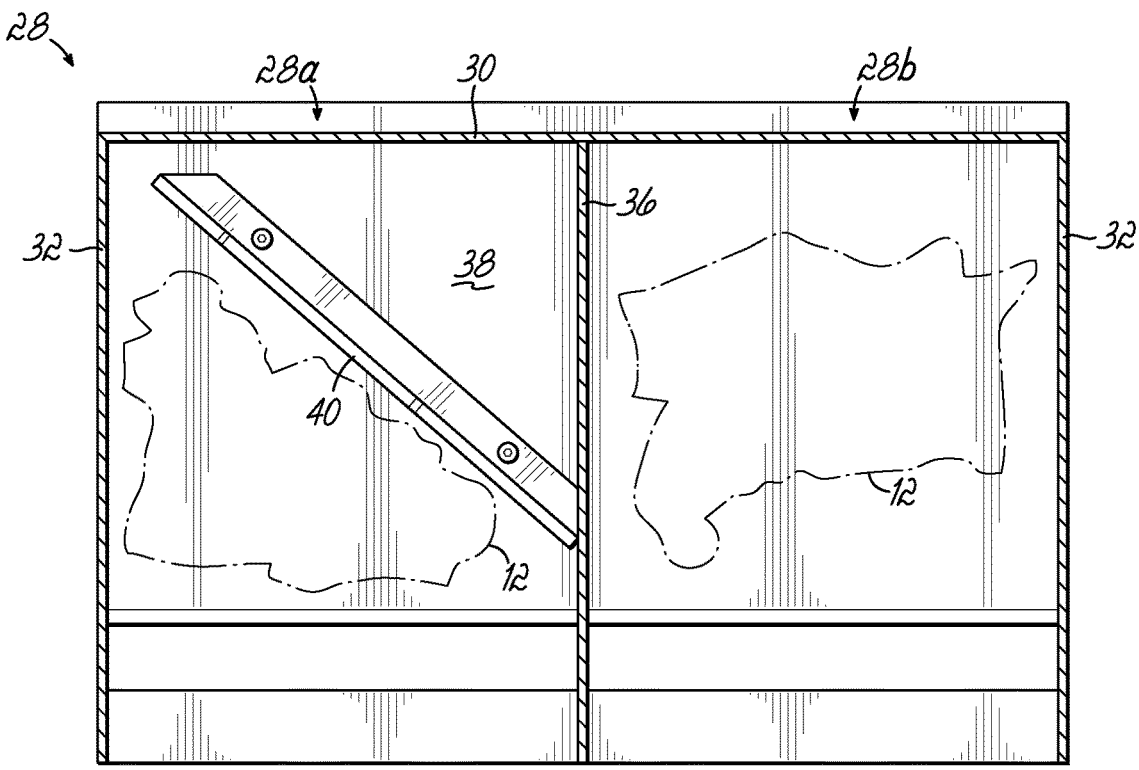
FIG. 10B is a top elevational view of the return portal and diverter of FIG. 9.
Figure 10C:
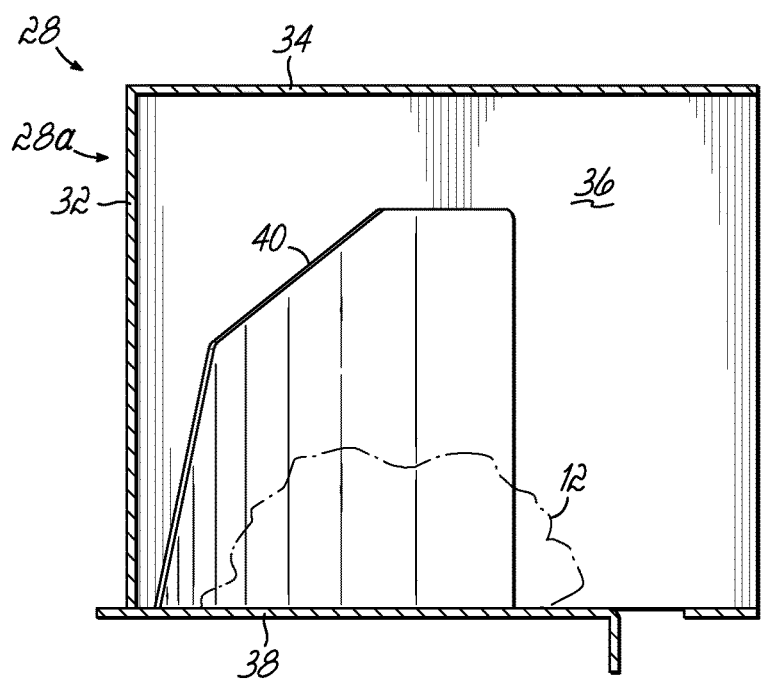
FIG. 10C is a side elevational view of the return portal and diverter of FIG. 9.

One aspect of various embodiments of this invention is a diverter 40 which is positioned in one or both of the portions 28a, 28b of the return portal 28. The diverter 40 is angled obliquely relative to the central partition 36 and the back wall 30 of the return portal 28 to guide the items 12 in that potion of the return portal 28 as they fall into the collection area 22. The diverter 40 assists in distributing the items 12 in the collection area 22 to avoid a mounded accumulation of the scrubs 12 or other items into a higher pile 42 in the collection area 22. The diverter 40 directs the returned scrubs 12 toward the perimeter of the collection area 22 so that they do no accumulate as quickly in the center of the collection area 22 directly below the return portal 28. As shown in FIG. 8, collection area 22a may have a pile 42a and collection area 22b may have a pile 42b, each of which contains items 12 from portions 28a, 28b, respectively, as a result of the diverter 40 and separate portions 28a, 28b.

Figure 2:
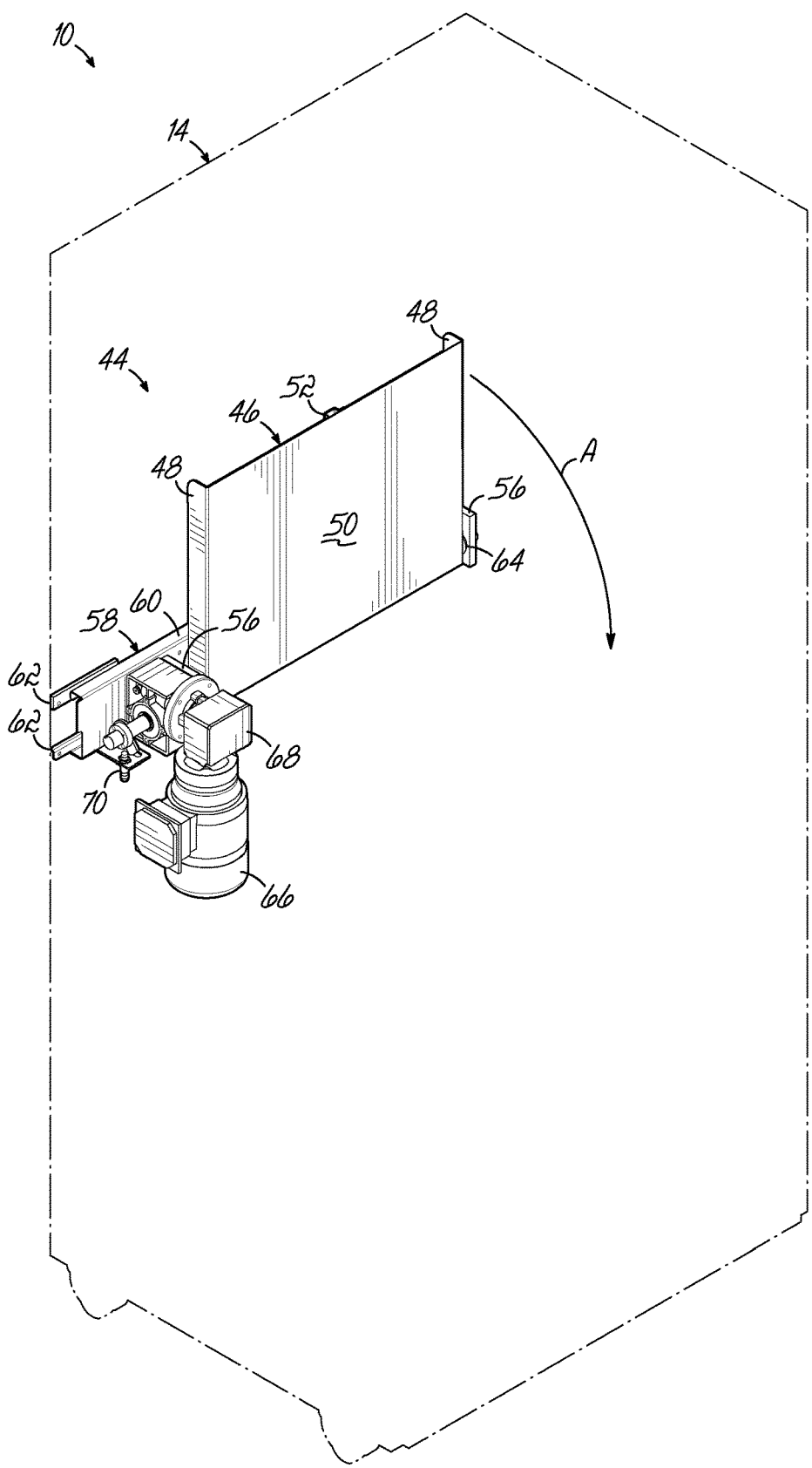
FIG. 2 is a perspective view of a compactor assembly within the returns cabinet according to one embodiment of this invention.
Figure 3:
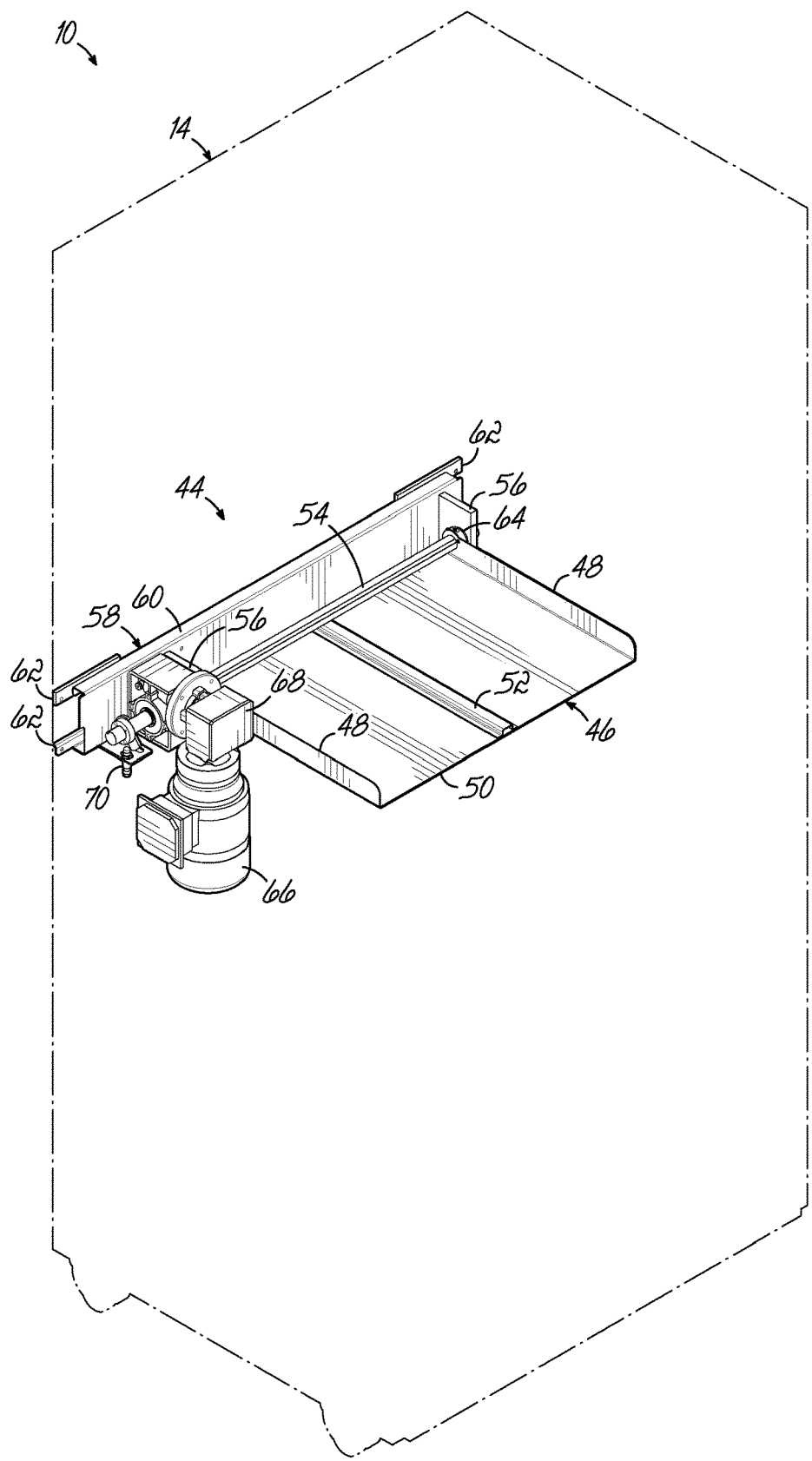
FIG. 3 is a view similar to FIG. 2 with the compactor assembly in a down or compacting position.
Figure 4:
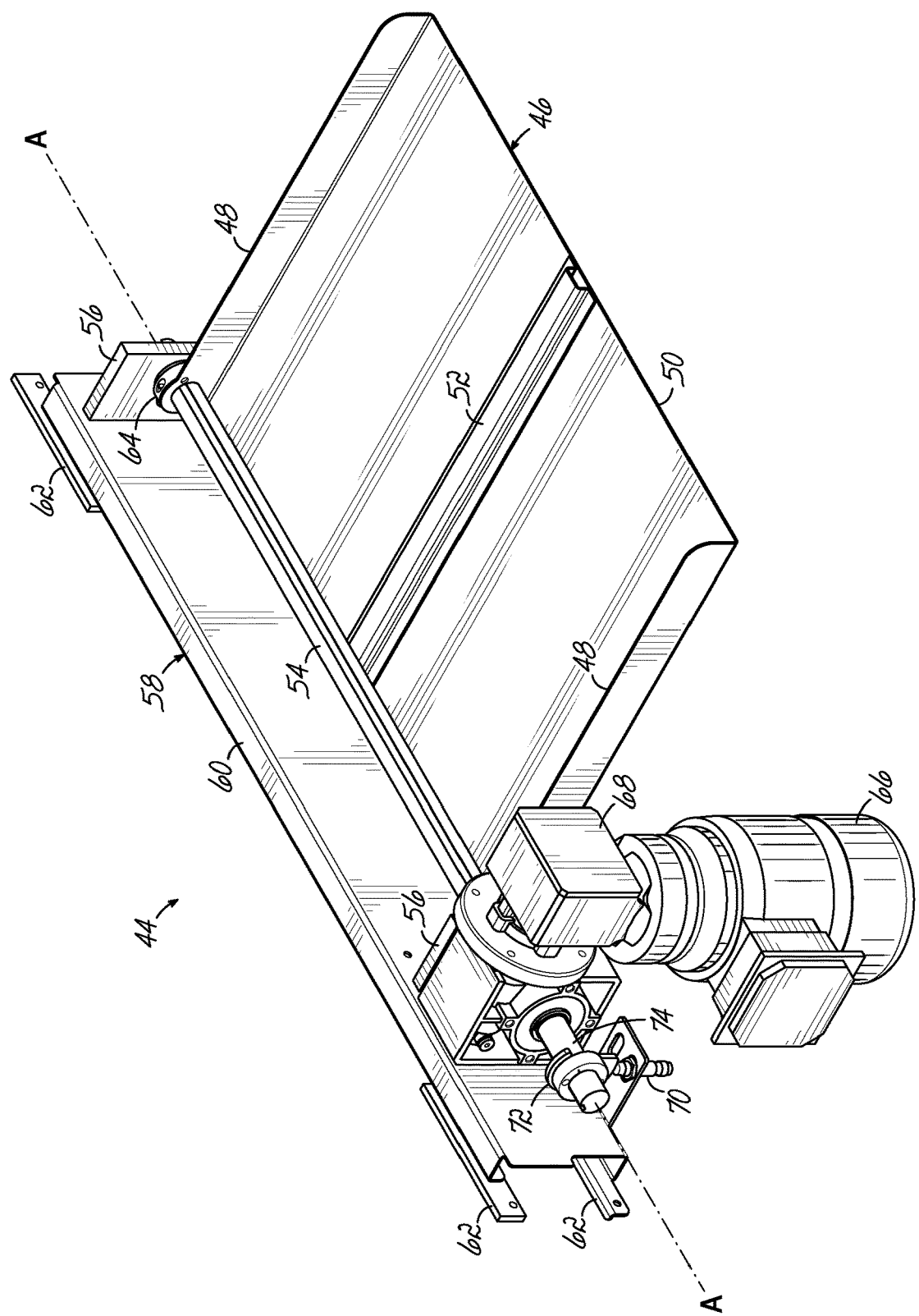
FIG. 4 is an enlarged perspective view of the compactor assembly of FIG. 3.

Referring to FIGS. 2-4, another aspect of this invention is a compactor assembly 44 for compacting the pile 42 of returned items 12 in the collection area 22. According to one embodiment, the compactor assembly 44 includes a paddle 46 having a pair of upturned lips 48 on opposite side edges thereof. The paddle 46 has a generally planar bottom face 50 as shown most clearly in FIG. 2. Positioned equal distance between the upturned lips 48 is a rib 52 for added strength and rigidity to the paddle 46. According to the embodiment shown in FIGS. 2-4, the paddle 46 has a generally rectangular bottom surface 50. As shown in FIG. 2, the paddle 46 is oriented generally vertically at rest and pivots downwardly in the direction of arrow A to compact returned items 12 in the collection area 22 as shown generally in FIG. 7C. As shown most clearly in FIGS. 3 and 4, a shaft 54 is mounted between the upturned lips 48 at a proximal edge of the paddle 46. The shaft 54 extends between a pair of flanges 56 projecting from a support carriage 58. The support carriage 58 includes a bulkhead 60 mounted on upper and lower brackets 62. The brackets 62 are mounted on the interior of the cabinet housing 14 and support the bulkhead 60 of the compactor assembly 44.

The shaft 54 is mounted to the paddle 46 for pivotal movement between a generally vertical rest position and a generally horizontal compacting position as shown in FIG. 3. The shaft 54 is coupled to a journal 64 at each flange 56 for pivotal movement. A motor 66 is coupled to the carriage 58 at one end of the shaft 54 as shown clearly in FIGS. 2-4. The motor 66 operates through a gear box 68 to pivot the paddle 46 downwardly and upwardly.

Figure 6:
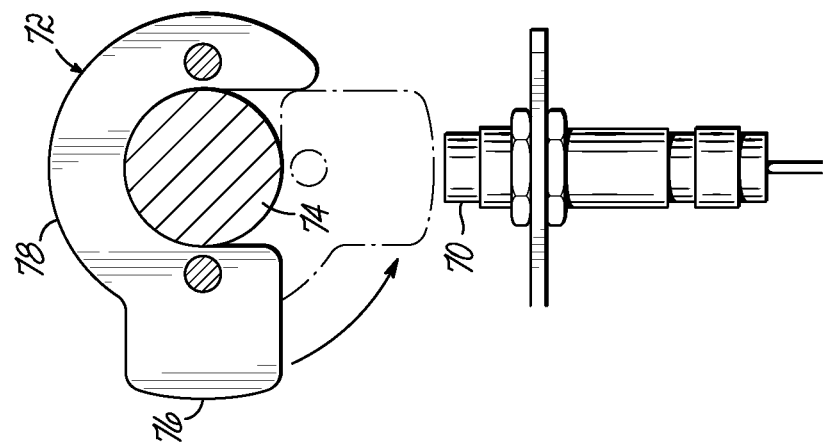
FIG. 6 is an enlarged side elevational view of the compactor assembly of FIG. 4.
Figure 5:
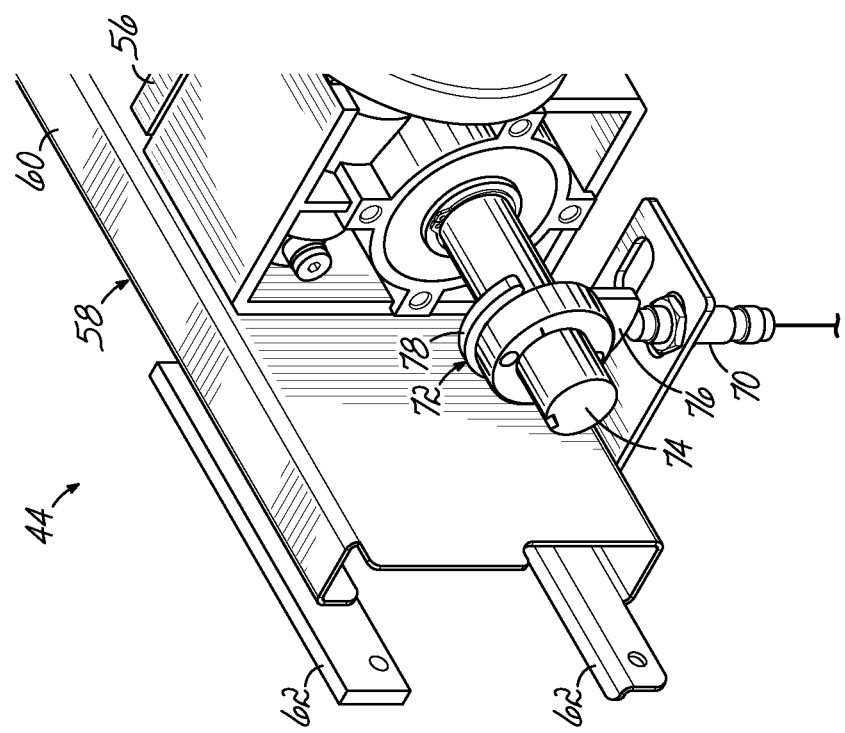
FIG. 5 is an enlarged perspective view of a portion of the compactor assembly of FIG. 4.

As shown most clearly in FIGS. 5 and 6, a proximity sensor 70 is mounted on the carriage 58 and directed upwardly toward a cam 72 mounted on an outboard extension 74 of the shaft 54. The cam 72 has a projection 76 extended radially outwardly relative to the remainder of the outer circumference 78 of the cam 72 as shown in FIG. 6. Depending on the rotation of the shaft 54 for the pivotal movement of the paddle 46 the projection 76 on the cam 72 is positioned in a close relationship with the proximity sensor 70 thereby indicating the angular orientation of the shaft 54 and the paddle 46 mounted thereto. In the unlikely event of a failure of the motor 66, the proximity sensor 70 and the associated projection 76 provide a fail safe measure to the operation of the compactor assembly 44.

Figure 7D:
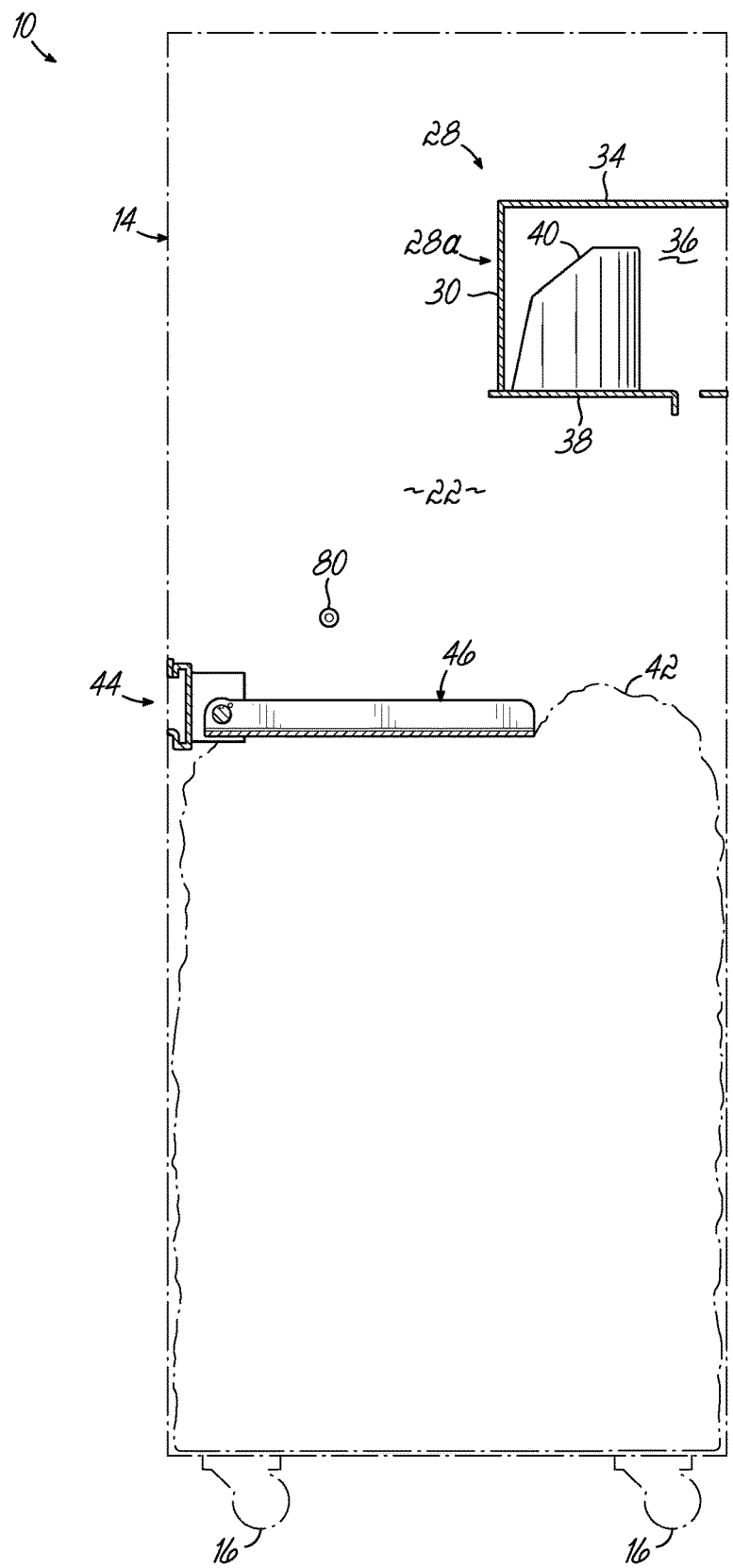

Referring to FIGS. 7A-7D, sequential operation of the compactor assembly 44 is shown. A photo electric eye sensor 80 is positioned relative to the collection area 22 such that when the accumulated pile 42 of returned scrubs 12 blocks or occludes the photo sensor 80 as in FIG. 7C, the controller triggers the paddle 46 to move from the rest or generally vertical position downwardly in the direction of arrow B as shown in FIG. 7C to thereby compact the accumulated pile 42 of scrubs 12 in the collection area 22 as shown in FIG. 7D. The paddle 46 pivots about a pivot axis A (FIG. 4) coincident with the shaft 54 to and between the vertical and horizontal positions. The location of the shaft 54 and the pivot axis A is fixed as shown by comparing its position in FIGS. 7A-7D. The paddle 46 compacts the accumulated pile 42 of scrubs 12 so that the photo sensor 80 is no longer blocked thereby indicating additional scrubs 12 may be deposited into the collection area 22. Continued accumulation of scrubs 12 eventually will result in the compacting operation not being able to clear the photo eye sensor 80 thereby indicating to the controller that the collection area 22 is full and needs to be emptied. The controller may then provide a signal to a user that the collection area 22 is full and the accumulated scrubs 12 need to be emptied from the collection area 22.

Advantageously, the generally planar and rectangular surface 50 of the paddle 46 engages a larger surface area of the accumulated pile 42 of returned scrubs 12 thereby providing a more effective compacting operation. Coverage by the generally planar surface of the paddle 46 provides a more effective and efficient compacting process on the accumulated pile 42 than known systems.

According to various embodiments of the compactor assembly 44 according to this invention, the number of scrubs 12 which may be retained in the collection area 22 increases from approximately 132 garments without the compactor assembly 44 and diverter 40 to approximately 250 garments with the compactor assembly 44 and diverter 40 thereby providing a significant increase in the capacity of the collection area 22 prior to being emptied. Moreover, in one embodiment of the paddle 46 approximately 84.4 pounds of force is delivered by the paddle 46 with a two foot lever arm at 42.2 pounds per foot of force. In other embodiments, 104.2 pounds of force can be delivered by the paddle 46 or 96.4 pounds of force in other embodiments.

In various embodiments of this invention, the compactor assembly 44 may or may not be integrated with the dispensing system controller. As a result of the paddle 46 and diverter 40 according to various embodiments of this invention, capacity for accepting scrubs 12 in the collection area may increase on the average of 160 percent.

From the above disclosure of the general principles of this invention and the preceding detailed description of at least one embodiment, those skilled in the art will readily comprehend the various modifications to which this invention is susceptible. Therefore, we desire to be limited only by the scope of the following claims and equivalents thereof.

We claim:

1. A system for receiving reusable items for subsequent processing and reuse, the system comprising:
 a housing;
 a collection area defined within a lower portion of the housing;
 a portal in the housing through which the items may be received into the housing;
 a door selectively covering the portal to selectively permit and prevent access to the collection area in the housing;
 a data entry device coupled to the door by which a user may open the door by entering date into the data entry device;
 a compactor assembly within the housing positioned superjacent to the collection area to selectively compact a plurality of the items within the collection area; and
 a paddle as part of the compactor assembly, the paddle being mounted in the housing for movement pivotally about a fixed axis to and between a rest position and a compacting position, the paddle contacting and compacting the plurality of items within the collection area when in the compacting position;
 wherein the fixed axis is at a first position when the paddle is in the rest position and a second position when in the compacting position and the first and second positions are at a same location within the housing;
 wherein the paddle has a generally planar face which contacts and compacts the plurality of items within the collection area when in the compacting position to allow for additional items to be received into the collection area after the paddle has returned from the compacting position to the rest position a diverter positioned in the portal to direct at least some of the items received therethrough into the collection area; wherein the portal further comprises a partition dividing the portal into first and second portal portions, each of which is adapted to receive items therein;

wherein the diverter is positioned in the first portal portion.

2. The system of claim 1 further comprising:

a sensor positioned within the housing relative to the collection area to identify when the plurality of items in the collection area has reached a predefined height after which the paddle moves from the rest position toward the compacting position thereby compacting the plurality of items to a level below the predefined height.

3. The system of claim 1 wherein the paddle is generally vertical when in the rest position and generally horizontal when in the compacting position.

4. The system of claim 1 wherein the paddle pivots through an are of about 900 to and from the rest position and the compacting position.

5. The system of claim 1, wherein the items received in the first portal portion are deposited into a first portion of the collection area and the items received in the second portal portion are deposited into a second portion of the collection area, the second portion being spaced from the first portion of the collection area.

6. A system for receiving reusable items for subsequent processing and reuse, the system comprising:

a housing;

a collection area defined within a lower portion of the housing;

a portal in the housing through which the items may be received into the housing;

a door selectively covering the portal to selectively permit and prevent access to the collection area in the housing;

a data entry device coupled to the door by which a user may open the door by entering date into the data entry device;

a compactor assembly within the housing positioned superjacent to the collection area to selectively compact a plurality of the items within the collection area;

a paddle as part of the compactor assembly, the paddle being mounted in the housing for movement pivotally about a fixed axis to and between a rest position and a compacting position, the paddle contacting and compacting the plurality of items within the collection area when in the compacting position;

wherein the fixed axis is at a first position when the paddle is in the rest position and a second position when in the compacting position and the first and second positions are at a same location within the housing;

wherein the paddle has a generally planar face which contacts and compacts the plurality of items within the collection area when in the compacting position to allow for additional items to be received into the collection area after the paddle has returned from the compacting position to the rest position;

a sensor positioned within the housing relative to the collection area to identify when the plurality of items in the collection area has reached a predefined height after which the paddle moves from the rest position toward the compacting position thereby compacting the plurality of items to a level below the predefined height; and a diverter positioned in the portal to direct at least some of the items received therethrough into the wherein the portal further comprises a partition dividing the portal into first and second portal portions, each of which is adapted to receive items therein; wherein the diverter is positioned in the first portal portion; wherein the items received in the first portal portion are deposited into a first portion of the collection area and the items received in the second portal portion are deposited into a second portion of the collection area, the second portion being spaced from the first portion of the collection area.

7. The system of claim 6 wherein the paddle is generally vertical when in the rest position and generally horizontal when in the compacting position.

8. The system of claim 6 wherein the paddle pivots through an are of about 90° to and from the rest position and the compacting position.

9. The system of claim 7 wherein the items are scrubs.

10. The system of claim 7 further comprising:

a collection door in the housing for access to the collection area and through which the items may be retrieved from the collection area.

\* \* \* \* \*